US011160523B2

(12) United States Patent
Jackson et al.

(10) Patent No.: US 11,160,523 B2
(45) Date of Patent: Nov. 2, 2021

(54) SYSTEMS AND METHODS FOR CARDIAC IMAGING

(71) Applicant: GE Precision Healthcare LLC, Milwaukee, WI (US)

(72) Inventors: John Irvin Jackson, Brookfield, WI (US); John Londt, Oconomowoc, WI (US); Darin Robert Okerlund, Muskego, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 109 days.

(21) Appl. No.: 16/588,945

(22) Filed: Sep. 30, 2019

(65) Prior Publication Data
US 2021/0093277 A1 Apr. 1, 2021

(51) Int. Cl.
*A61B 6/00* (2006.01)
*A61B 6/03* (2006.01)
*A61B 6/04* (2006.01)

(52) U.S. Cl.
CPC .............. *A61B 6/503* (2013.01); *A61B 6/032* (2013.01); *A61B 6/5205* (2013.01); *A61B 6/5264* (2013.01); *A61B 6/541* (2013.01); *A61B 6/0407* (2013.01); *A61B 6/467* (2013.01); *A61B 6/481* (2013.01)

(58) Field of Classification Search
CPC ....... A61B 6/503; A61B 6/541; A61B 6/0407; A61B 6/5264; A61B 6/467; A61B 6/032; A61B 6/5205
See application file for complete search history.

(56) References Cited

U.S. PATENT DOCUMENTS

| 5,668,846 A * | 9/1997 | Fox ..................... A61B 6/464 378/4 |
| 7,233,644 B1 * | 6/2007 | Bendahan ............ G01N 23/046 378/57 |
| 2006/0247518 A1 * | 11/2006 | Boing .................. A61B 6/481 600/431 |
| 2007/0172024 A1 * | 7/2007 | Morton ................ A61B 6/5235 378/10 |
| 2019/0266760 A1 | 8/2019 | Jackson et al. |

OTHER PUBLICATIONS

Boudoulas, H. et al., "Linear Relationship Between Electrical Systole, Mechanical Systole, and Heart Rate," Chest, vol. 80, No. 5, Nov. 1981, 5 pages.
Chung, C. et al., "Duration of diastole and its phases as a function of heart rate during supine bicycle exercise," AJP Heart and Circulatory Physiology, vol. 287, No. 5, Dec. 2004, 6 pages.

* cited by examiner

*Primary Examiner* — Chih-Cheng Kao

(57) ABSTRACT

Methods and systems are provided for generating a diagnostic cardiac image using a CT system without ECG gating techniques. In one example, a method for an imaging system includes determining a scanning duration for scanning a heart of a patient with the imaging system based on a heart rate of the patient, scanning the patient with the imaging system for the scanning duration, the scanning commenced independent of a current phase of a cardiac cycle of the heart of the patient, and reconstructing an image from data acquired during the scanning.

17 Claims, 4 Drawing Sheets

SYSTEMS AND METHODS FOR CARDIAC IMAGING

FIELD

Embodiments of the subject matter disclosed herein relate to medical imaging systems, and more particularly, to cardiac computed tomography (CT).

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures).

BRIEF DESCRIPTION

In an embodiment, a method for an imaging system includes determining a scanning duration for scanning a heart of a patient with the imaging system based on a heart rate of the patient, scanning the patient with the imaging system for the scanning duration, the scanning commenced independent of a current phase of a cardiac cycle of the heart of the patient, and reconstructing an image from data acquired during the scanning.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
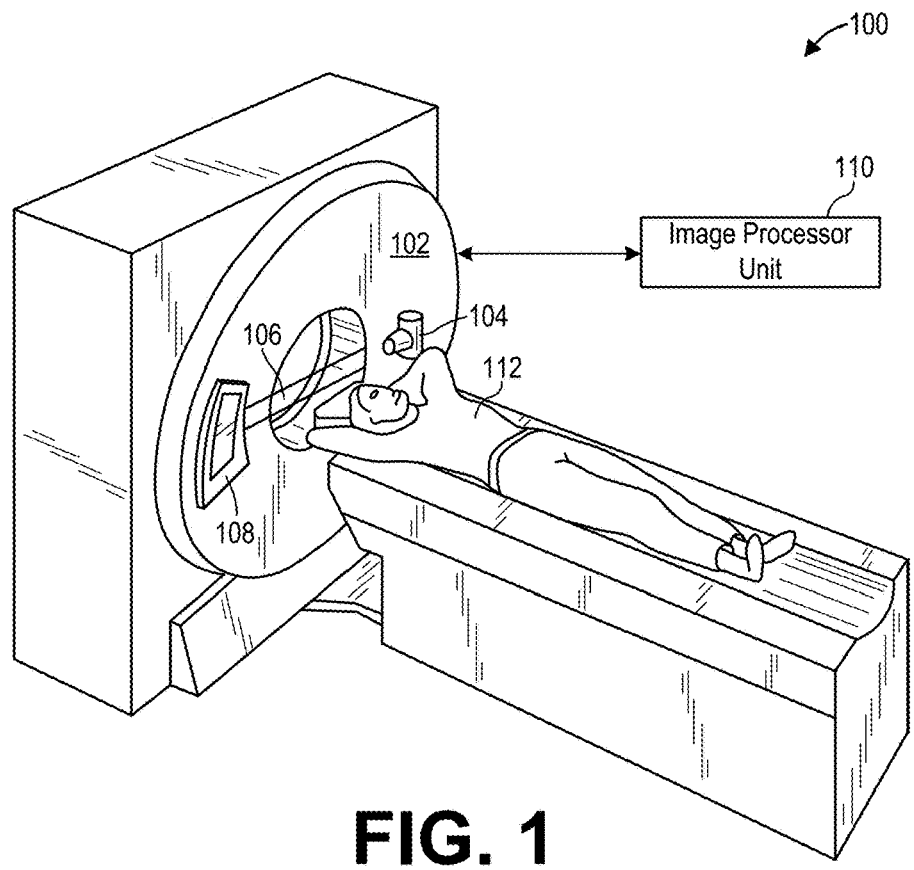
FIG. 1 shows a pictorial view of an imaging system according to an embodiment.

Cardiac computed tomography (CT) is a heart-imaging modality that uses CT technology with or without intravenous contrast dye to visualize the heart anatomy, coronary circulation, and/or great vessels. As heart rates may range from 50 to more than 100 beats per minute (bpm), the main challenge in cardiac CT is temporal resolution or imaging fast enough to capture an image that is not blurred by the motion of the heart. Thus, the faster the heart beats, the smaller the window between contractions becomes, thereby limiting the time in which a clear or diagnostic image may be obtained. Various techniques are used to improve the temporal resolution during CT scans and minimize imaging artifacts caused by cardiac motion, such as acquiring data at specific times relative to electrocardiogram (ECG) events, such as the ECG R-wave, commonly known as ECG gating, ECG gate-keeping, or ECG triggering.

The least cardiac motion occurs during diastole, after the ventricles have passively filled and before the atria contract. As such, current methods for acquiring cardiac CT data involve scanning when a patient's heart is in ventricular diastole, which is traditionally determined via electrocardiography. Another good time for scanning where there is relatively little motion is at the end of systole, when the heart is near the end of its mechanical contraction. A patient's ECG waveform, in particular the R-wave which aids in delineating between diastole and systole (active pumping), may be used to control the precise timing of when x-rays are turned on/off as well as control the time window of data used to reconstruct a cardiac CT image so that motion is minimized. Thus, by targeting x-ray exposure to a particular time window relative to the ECG R-wave, the radiation dose may be reduced by only acquiring data sufficient to ensure, with reasonable confidence, at least one image set with minimal motion.

However, ECG gate-keeping for CT systems demands time and has associated costs. Electrode patches must be placed on or near the patient's chest which may require removal or adjustment of clothing, preparation of the application sites, and cause the patient minor discomfort. Additionally, on some individuals, such as trauma or burn patients, it may be difficult to successfully attach ECG electrodes. ECG leads, which are best made out of a radiotranslucent material, such as carbon fiber, are expensive and sometimes need to be replaced. Further, hardware must be used to detect and record the ECG signal, as well as to detect the R-wave within that signal. Using an ECG in conjunction with a cardiac CT system also demands a communication mechanism to transmit the ECG signal to a system controller which has to be programmed to use that signal to appropriately control the CT system in a manner that is synchronized to the ECG and R-wave. Thus, using an ECG has costs for each exam, costs for the CT system, and requires set-up time for each patient. Further, ECG R-wave detection may not always be correct, such as when elevated T-waves are misinterpreted as R-waves. This can cause errors in heart rate prediction and in both acquisition and reconstruction timing.

Thus, according to embodiments disclosed herein, a cardiac CT scan may be performed for less than a heartbeat without ECG gate-keeping. For example, the CT scan may be performed with an x-ray exposure that is longer than a minimum x-ray exposure duration demanded to reconstruct a single image and less than an x-ray duration demanded to acquire and reconstruct images depicting a full heartbeat. The use of this duration to scan and reconstruct a cardiac image may result in an image with minimal motion, or an amount of motion that does not significantly impede the intended clinical diagnosis, while minimizing radiation exposure to the patient.

In one embodiment, scanning may be performed to ensure at least the end of systole or middle of diastole is included within the acquired projection data. The timing of end-systole and mid-diastole may be specifically determined based on a patient's heart rate range and scanning carried out long enough to ensure that one of these times (e.g., the end of systole or middle of diastole) is centered within the data acquisition window regardless of what phase of the cardiac cycle the patient's heart is in when scanning commences. This may be achieved by scanning for a duration comprised of the longest non-diagnostic interval between these two times (e.g., the end of systole or middle of diastole) and the time required to acquire sufficient data to reconstruct an image in a single phase.

The ability to perform a cardiac CT scan without ECG gate-keeping as described above, thereby decreasing costs, time, and the amount of patient radiation exposure associated with current methods of heart imaging, may be facilitated by a combination of factors. First, scanning may be performed with CT scanning technology that allows for whole-heart coverage, in which a full image of the heart may be reconstructed from a single window of time rather than having to generate volumes of cross-sections at the same portion of the cardiac cycle. Second, the use of a CT system having relatively fast gantry speeds (e.g., faster than 1 rotation/second) and multiple x-ray sources (offset in the angular direction) may reduce the amount of motion during a reconstruction window, thereby reducing image motion artifacts and allowing a wider range of heart phases to be diagnostically useful. Third, reconstruction techniques may be used which generate images with lower noise than previous methods, thereby allowing diagnostic images to be generated with a lower flux of radiation per reconstruction time window. Thus, reasonable and acceptable radiation dose levels may be maintained for longer exposures. Fourth, various motion correction algorithms for image reconstruction may be utilized, allowing for phases that would have previously generated non-diagnostic images (due to heart movement) to be motion corrected to generate diagnostic images. And, Fifth, advanced analysis algorithms may be used to analyze a range of acquired cardiac CT scan data and determine which subrange has the least amount of motion. These factors facilitate the use of a CT system to acquire high-quality, low motion cardiac images without the use of an ECG signal.

Current cardiac CT data may be acquired in the absence of an ECG signal, such as in older methods of helical scanning in which the scan is performed for the duration of a single breath-hold, with time windows for image reconstruction determined after the exposure. However, this antiquated version of helical scanning subjects the patient to undue radiation. Additionally, CT systems that use various methods of ECG gate-keeping have an integrated back-up to handle situations in which the ECG signal is lost immediately before the intended x-ray exposure. In these situations, cardiac CT data is acquired over a little more than a heartbeat or a heartbeat of a nominal duration (e.g., one second which would correspond to a heart rate of sixty bpm). However, this is only a fail-safe method and still subjects the patient to undue radiation.

The following description relates to various embodiments of medical imaging systems. In particular, systems and methods are provided for using a CT imaging system to generate a diagnostic cardiac image based on a model of heart rate motion. An example of a CT imaging system that may be used to acquire images in accordance with the present techniques is provided in FIGS. 1 and 2. FIG. 3A provides an example of an ECG waveform that may be used to gate various steps that may be performed by CT imaging systems such as those presented in FIGS. 1 and 2 during cardiac imaging. FIG. 3B depicts non-diagnostic intervals between cardiac phases on the example ECG waveform presented in FIG. 3A. A method for generating a diagnostic cardiac image using a CT system without ECG gate-keeping is outlined in FIG. 4.

Though a CT system is described by way of example, it should be understood that the present techniques may also be useful when applied to other imaging modalities, such as fluoroscopy, C-arm angiography, hybrid imaging systems (e.g., CT/PET) and so forth. The present discussion of a CT imaging modality is provided merely as an example of one suitable imaging modality.

FIG. 1 illustrates an exemplary CT system 100 configured for CT imaging. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray source 104 configured to project a beam of x-ray radiation 106 for use in imaging the subject 112. Specifically, the x-ray source 104 is configured to project the x-rays 106 towards a detector array 108 positioned on the opposite side of the gantry 102. Although FIG. 1 depicts only a single x-ray source 104, in certain embodiments, multiple x-ray radiation sources and detectors may be employed to project a plurality of x-rays 106 for acquiring projection data corresponding to the patient at different energy levels. In some embodiments, the x-ray source 104 may enable dual-energy gemstone spectral imaging (GSI) by rapid kVp switching. In some embodiments, the x-ray detector employed is a photon-counting detector which is capable of differentiating x-ray photons of different energies. In other embodiments, two sets of x-ray tube-detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some known CT imaging system configurations, a radiation source projects a cone-shaped beam which is collimated to lie within an X-Y-Z plane of a Cartesian coordinate system and generally referred to as an "imaging plane." The radiation beam passes through an object being imaged, such as the patient or subject 112. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In some CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view." A "scan" of the object includes a set of views made at different gantry angles, or view angles, during one revolution of the radiation source and detector. It is contemplated that the benefits of the methods described herein accrue to medical imaging modalities other than CT, so as used herein the term view is not limited to the use as described above with respect to projection data from one gantry angle. The term "view" is used to mean one data acquisition whenever there are multiple data acquisitions from different angles, whether from a CT, PET, or SPECT acquisition, and/or any other modality including modalities yet to be developed as well as combinations thereof in fused embodiments.

The projection data is processed to reconstruct an image that corresponds to a two-dimensional slice taken through the object. One method for reconstructing an image from a set of projection data is referred to in the art as the filtered back projection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

Figure 2:
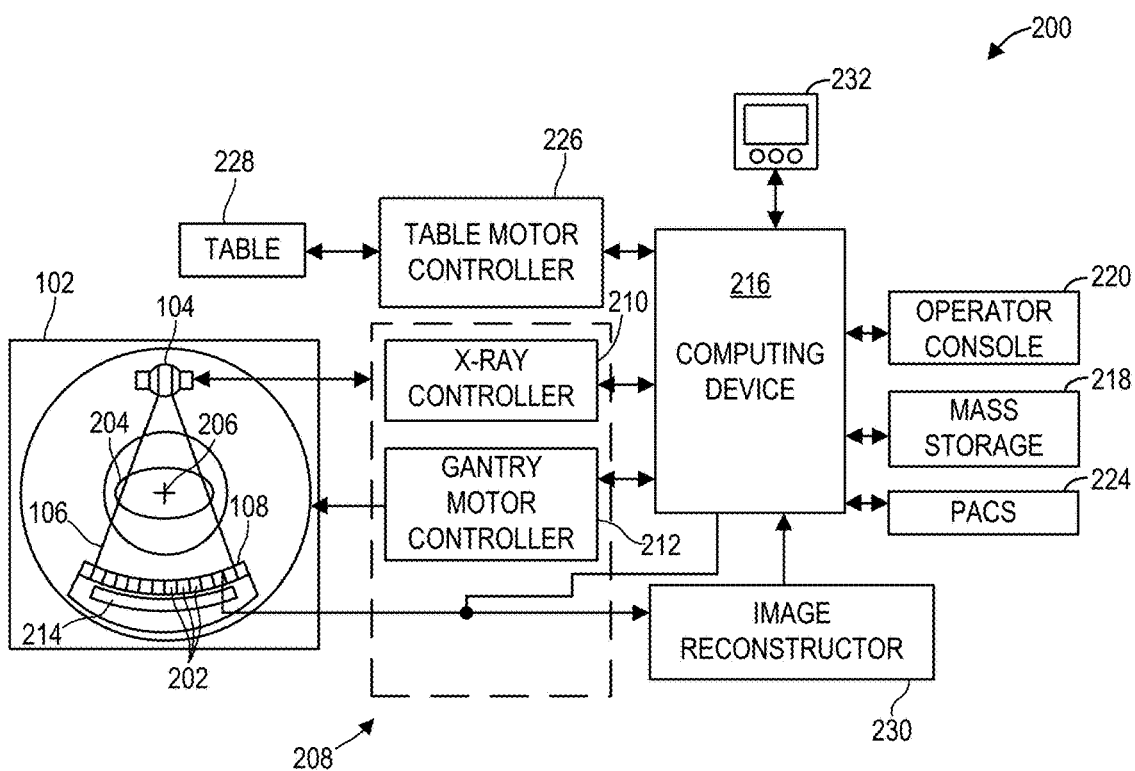
FIG. 2 shows a block schematic diagram of an exemplary imaging system according to an embodiment.
Figure 3A:
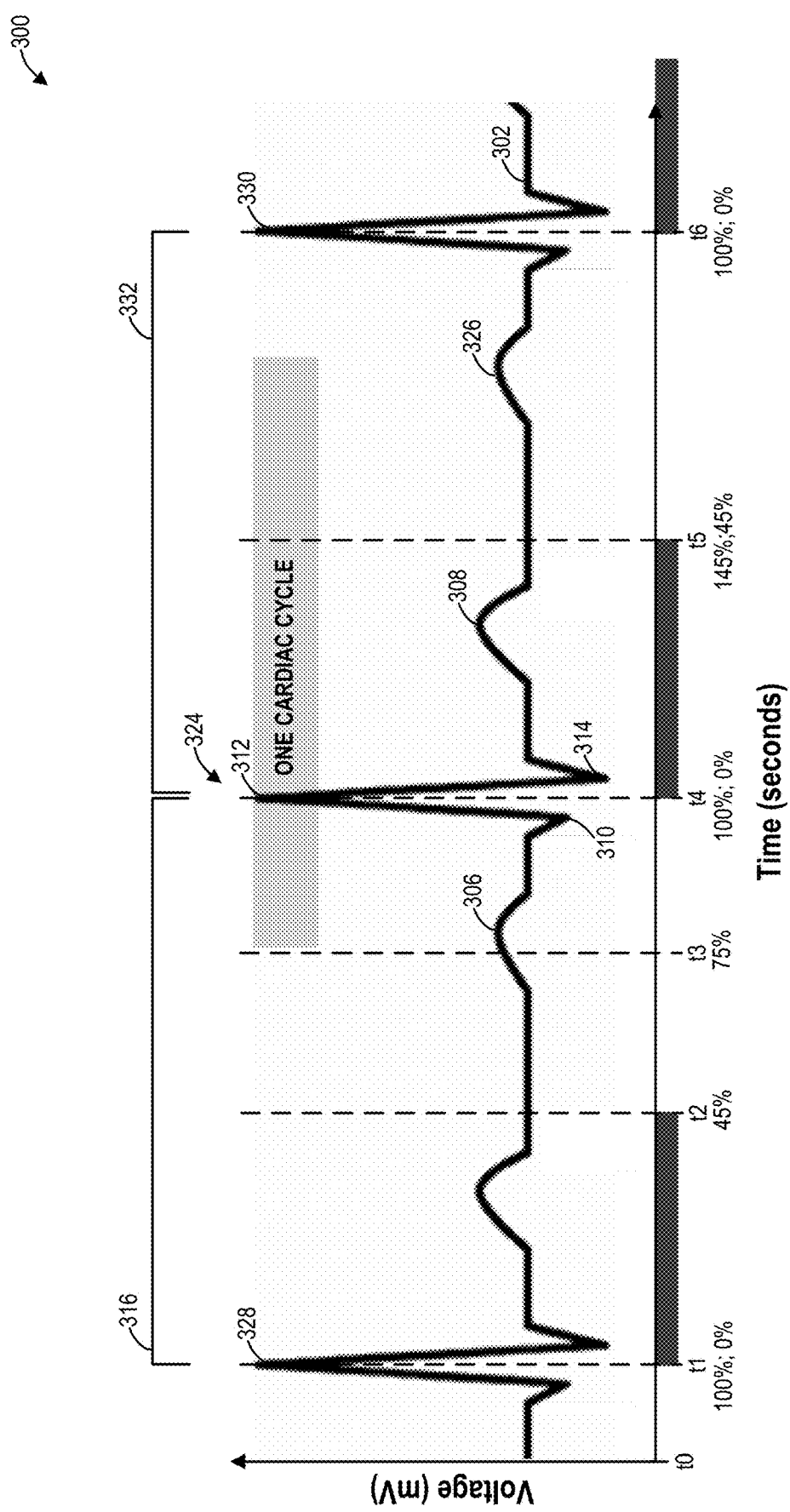
FIG. 3A depicts an example electrocardiogram (ECG) waveform that may be used for imaging system gating.
Figure 3B:
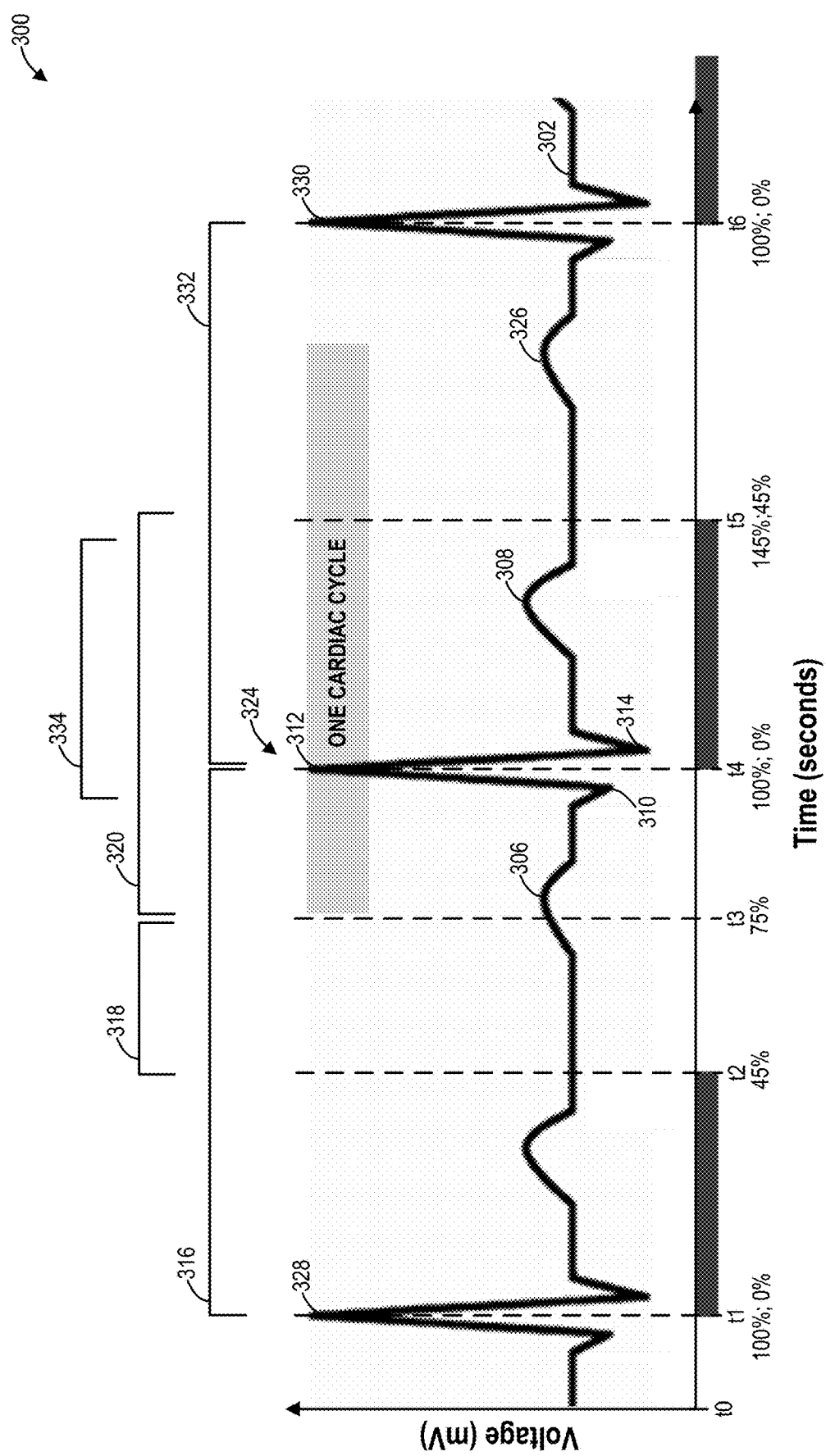
FIG. 3B depicts non-diagnostic intervals within the cardiac cycles of the example ECG waveform presented in FIG. 3A.

FIG. 2 illustrates an exemplary imaging system 200 similar to the CT system 100 of FIG. 1. In accordance with aspects of the present disclosure, the imaging system 200 is configured for imaging a subject 204. In one embodiment, the imaging system 200 includes the detector array 108 (see FIG. 1). The detector array 108 further includes a plurality of detector elements 202 that together sense the x-ray beams 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may comprise photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of the two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the imaging system 200 either includes or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 228 which may comprise a motorized table. Particularly, the table motor controller 226 moves the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230.

The various methods and processes described further herein may be stored as executable instructions in non-transitory memory on a computing device in imaging system 200. In one embodiment, image reconstructor 230 may include such executable instructions in non-transitory memory, and may apply the methods described herein to reconstruct an image from scanning data. In another embodiment, computing device 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230 and computing device 216.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

The CT system 100 and imaging system 200 of FIGS. 1 and 2, respectively, may use ECG gating techniques to better achieve motion-free imaging of the heart thereby increasing the amount of diagnostic images gained during imaging. As a non-limiting example, FIGS. 3A and 3B provide a plot 300 of an example temporal window of an ECG waveform 302 depicting electrical activity of a heartbeat as monitored by electrocardiography and that may be used to determine when to initiate table motion and/or turn x-rays on or off in the imaging systems described above. The voltage (mV) of the waveform 302 produced by the heartbeat, on the Y-axis, is shown as a function of time (seconds) on the X-axis.

During ECG monitoring, electrodes attached to a patient's skin detect electrical changes that are a consequence of cardiac muscle depolarization followed by repolarization during each cardiac cycle (a heartbeat). There are three main components of an ECG waveform, such as waveform 302, which repeat as the heart beats: a P-wave 306, which represents the depolarization of the atria; a QRS complex 324, which represents ventricular depolarization; and a T-wave 308, which represents repolarization of the ventricles. The QRS complex 324 is comprised of three waves that occur in rapid succession: a Q-wave 310, which is an initial negative deflection in the QRS complex 324; followed by an R-wave 312 which is the first upward deflection after a P-wave, such as P-wave 306; and a S-wave 314, which is a negative deflection occurring just after an R-wave, such as R-wave 312. One cardiac cycle, as indicated on plot 300, may begin at P-wave 306, include QRS complex 324 and T-wave 308, and end at a subsequent P-wave 326, which represents the start of the next cardiac cycle. The next cardiac cycle may begin at subsequent P-wave 326 and follow the same pattern as described above as the heart continues to beat.

Generally, the relative timing of cardiac scans using CT systems that utilize ECG signals is based on R-waves, as R-waves are the easiest ECG wave to identify based on voltage/signal amplitude. The interval between two R-waves, or an R-R interval, may define whether a patient's heart is in ventricular systole or ventricular diastole based on phase, with phase herein being defined as a percentage of the way through an R-R interval. In plot 300, the grey boxes that line the X-axis indicate phases where the patient's heart is in ventricular systole. When the patient's heart is not in ventricular systole (as defined by the grey boxes lining the X-axis), the patient's heart is in ventricular diastole. The X-axis starts at time point 0, or t0. Thus, a first time point, t1, indicates a phase of 0% for an R-R interval 316 as defined by a first R-wave 328 and subsequent R-wave 312. A second time point, t2, indicates a phase of approximately 45% for R-R interval 316. A third time point, t3, indicates a phase of approximately 75% for R-R interval 316. A fourth time point, t4, indicates a phase of approximately 100% for R-R interval 316. Further, t4 also indicates a phase of 0% for an R-R interval 332 that succeeds R-R interval 316, with R-R interval 332 defined by R-wave 312 and a third R-wave 330. Thus, a fifth time point, t5, indicates a phase of approximately 45% for R-R interval 332. With respect to R-R interval 316, t5 indicates a phase of approximately 145%. A sixth time point, t6, indicates a phase of 100% for R-R interval 332 as well as a 0% phase for the next R-R interval as the pattern continues while the patient's heart beats. As shown in plot 300, ventricular systole occurs from t1 to t2, t4 to t5, and begins again at t6. Thus, ventricular systole roughly occurs between a phase of 0% to 45% and ventricular diastole from 45% to 100%. Mid-diastole, which is indicated by t3, occurs at a phase of roughly 75% and often has the least amount of motion for heart rates.

For ECG gated imaging, the CT scanner monitors the patient's ECG and is set to scan at a particular point in the cardiac cycle which is typically during diastole as the heart is moving the least. The CT scanner may interpret the ECG and determine a delay after a QRS complex to begin scanning. Once that point of delay has occurred, the ECG may trigger the CT scanner to start scanning. For example, in FIG. 3A, t5 may represent a point of delay after QRS complex 324 that triggers CT scanning so that the scan data includes some range of diastole for a given cardiac cycle.

However, the use of ECG R-waves for triggering cardiac CT scans and subsequently selecting images for reconstruction is not completely robust, having several logistical and technical challenges. For example, false triggers may occur from a T-wave or the presence of an atrial pacing spike occurring just before a QRS complex (such as QRS complex 324). Electrodes used for ECGs during cardiac CT scans are positioned such to accentuate R-waves and minimize T-waves. However, patients with a prominent T-wave often prove difficult to image as ECG mis-gating may occur from a triggering of the CT system by a T-wave rather than a QRS complex. Further, EGC gating for cardiac CT scans may be impaired in people with a low ECG signal. A low ECG signal may result from geometries that decrease signal to the ECG leads, such as in barrel chested patients with chronic obstructive pulmonary disease (COPD). Large pericardial effusion may also decrease the ECG signal. Further, a common ECG gating artifact, known as the magnetohydrodynamic effect, may occur when ions within the blood are transported through a magnetic field, inducing a voltage and distorting the ECG recording.

Thus, according to an embodiment of the subject matter disclosed herein, a cardiac CT scan may be performed where the scanning duration is based on a model of heart rate motion rather than ECG gate-keeping. The scanning may be commenced independent of any mechanism that determines the current phase of the cardiac cycle, such as independent of ECG input or independent of photoplethysmography (PPG) input, where PPG includes determining the timing of cardiac cycles via continuous monitoring of changes in blood volume in a portion of the peripheral microvasculature. By basing scan timing/data acquisition on a patient's heart rate, the radiation dose may be reduced by acquiring CT imaging information only over a duration wherein a predetermined or pre-selected phase or range of phases having minimal motion is guaranteed to be imaged. For example, scanning so that the end of systole or mid-diastole, as determined by a patient's heart rate range, is included within the projection data may ensure that a diagnostic image having little or no motion is generated. Accordingly, scanning may be performed to ensure at least one of a phase of 45% or a phase of 75% is included in the acquired projection data. However, when performing ECG-less CT scanning of the heart as described herein, the current phase of the patient's cardiac cycle when scanning commences is not known e.g., scanning is performed independent of the cardiac phase). Thus, scanning is carried out for long enough to ensure that, regardless of what phase of the cardiac cycle the patient's heart is in when scanning commences, at least a phase of 45% or 75% occurs during scanning and that the 45% or 75% phase occurs in the center of a data acquisition window sufficient to generate a single image so that an image of the heart at 45% or 75% may be reconstructed. The patient's cardiac cycle may thus be divided into two non-diagnostic intervals that are defined as the intervals between 45% and 75% and between 75% and the following 45%. The non-diagnostic intervals thus include a first non-diagnostic interval that spans from 45% to 75% and a second non-diagnostic interval that spans from 75% to 145% of the following R-R interval. While each of the non-diagnostic intervals include both diagnostic phases (e.g., the first diagnostic interval includes both 45% and 75%), as mentioned above, to reconstruct an image of a diagnostic phase, that phase needs to be centered in a data acquisition window. Thus, the diagnostic phase at the beginning of the interval is not sufficient to reconstruct an image of that phase, and additional scan time is added to the end of the non-diagnostic window to ensure that the diagnostic phase at the end of the interval can be reconstructed into an image. As such, scanning may occur independent of a current phase of a cardiac cycle (e.g., at the start of an R-R interval, during a P-wave, just after an S-wave).

If scanning commences during one of these non-diagnostic intervals, scanning has to be carried out long enough to ensure that the next diagnostic interval (e.g., 45% or 75%) is included in the scan, with enough data acquired to reconstruct an image from data acquired at/around 45% or 75%. Thus, a worst-case scenario would include scanning commencing at 76%. If scanning were to commence at 76%, scanning would need to be carried out until a phase of 145% is reached, with enough data acquisition before the scanning is terminated to ensure an image can be reconstructed from data acquired at 145%. Thus, the second non-diagnostic interval is the longest duration of time of scanning that is needed to ensure a diagnostic image can be generated. The duration of the second non-diagnostic interval may change as the heart rate changes, and thus the patient's longest duration of scanning time may be determined based on the patient's heart rate.

As shown in FIG. 3B, for a patient with diastole beginning at 45% and mid-diastole at 75%, the first non-diagnostic interval 318 includes 30% of an R-R interval. Alternatively, in the worst case scenario, the longest non-diagnostic interval 320 that will include either a phase of 45% or a phase of 75% may range from 75% of R-R interval 316 to 45% of R-R interval 332. Thus, the second non-diagnostic interval 320 includes 70% of an R-R interval. In a patient having a heart rate of 60 bpm, the second non-diagnostic interval 320 may be 700 msec. However, as explained above, additional scan time is included to ensure an image at 145% can be reconstructed if scanning commences at 76%, and this additional scan time may be a function of the specific CT system (e.g., a minimum amount of gantry rotation required to reconstruct one image) and/or image reconstruction or processing parameters (e.g., whether motion correction is going to applied). For example, the additional scan time may be the time for 240° of a gantry rotation (e.g., if motion correction is not going to be applied) to be completed or the time for 400° of gantry rotation to be completed (e.g., if motion correction is going to be applied).

Further, the application of motion correction may expand the range in which projection data is sufficient for generating a diagnostic image (e.g., expand one or both of the diagnostic intervals). Motion artifacts generally tend to be most pronounced at higher heart rates, but the use of a motion correction algorithm can reduce motion artifacts even in patients with a low and regular heart rate. Thus, motion correction may increase the range of phases that can produce a diagnostic image. For example, use of a motion correction algorithm may increase the nominally accepted phases of 45% and 75% to 40-55% and 70-90% so that a smaller acquisition window may be used to generate a diagnostic image thereby reducing patient exposure to radiation. As shown in FIG. 3B, if the phase ranges of 40-55% and 70-90% were determined sufficient for generating a diagnostic image, the longest non-diagnostic interval 334 may then range from 90% of R-R interval 316 to 140% of R-R interval 332. Thus, the worst case scenario for generating a diagnostic cardiac image may only require an acquisition window of 50% of an R-R interval, as compared to 70% without motion correction. Thus, for a patient having a heart rate of 60 bpm, the longest duration of scanning time to acquire an image at 40-55% or 70-90% may be 500 msec, relative to 700 msec for a scan where the images are not motion corrected (explained above). Reducing the duration of radiation to which the patient is exposed gives a corresponding reduction in the likelihood of radiation-induced health problems to the affected tissue of patients, which is especially important for young patients having cardiac diseases who are more likely to require repeated cardiac imaging sessions over a longer portion of their lives (relative to older patients or patients without cardiac disease). Further, by reducing the length of the acquisition window that may robustly generate a diagnostic cardiac image, lower gantry speeds may be used and, as such, the radiation dose to the patient may also be lowered. As an example, if a nominal exam used a gantry rotation time of 0.25 seconds and 1000 mA, then a motion-corrected scan may be performed with a gantry rotation time of 0.50 seconds and 500 mA. If both scans required the same time/phase duration for exposure to generate a diagnostic image, a patient undergoing a motion corrected scan would receive half the dose of radiation for the same result.

As explained above, the scanning duration as calculated herein includes the longest non-diagnostic interval (e.g., 75%-145%) plus an additional scan time that includes a minimum scanning duration that is required to be able to reconstruct a complete image. This minimum scanning duration is based on the gantry speed, as the minimum scanning duration may be a function of a gantry rotation (e.g., two-thirds of a rotation or a full rotation). If a lower gantry speed is used, the minimum scanning duration may increase. Thus, in order to maintain the total scanning duration as less than the time to complete a single heartbeat of the patient, the lowered gantry speed may only be implemented when the longest non-diagnostic interval is sufficiently short, as when the diagnostic intervals are lengthened when motion correction is applied to the reconstructed images.

Figure 4:
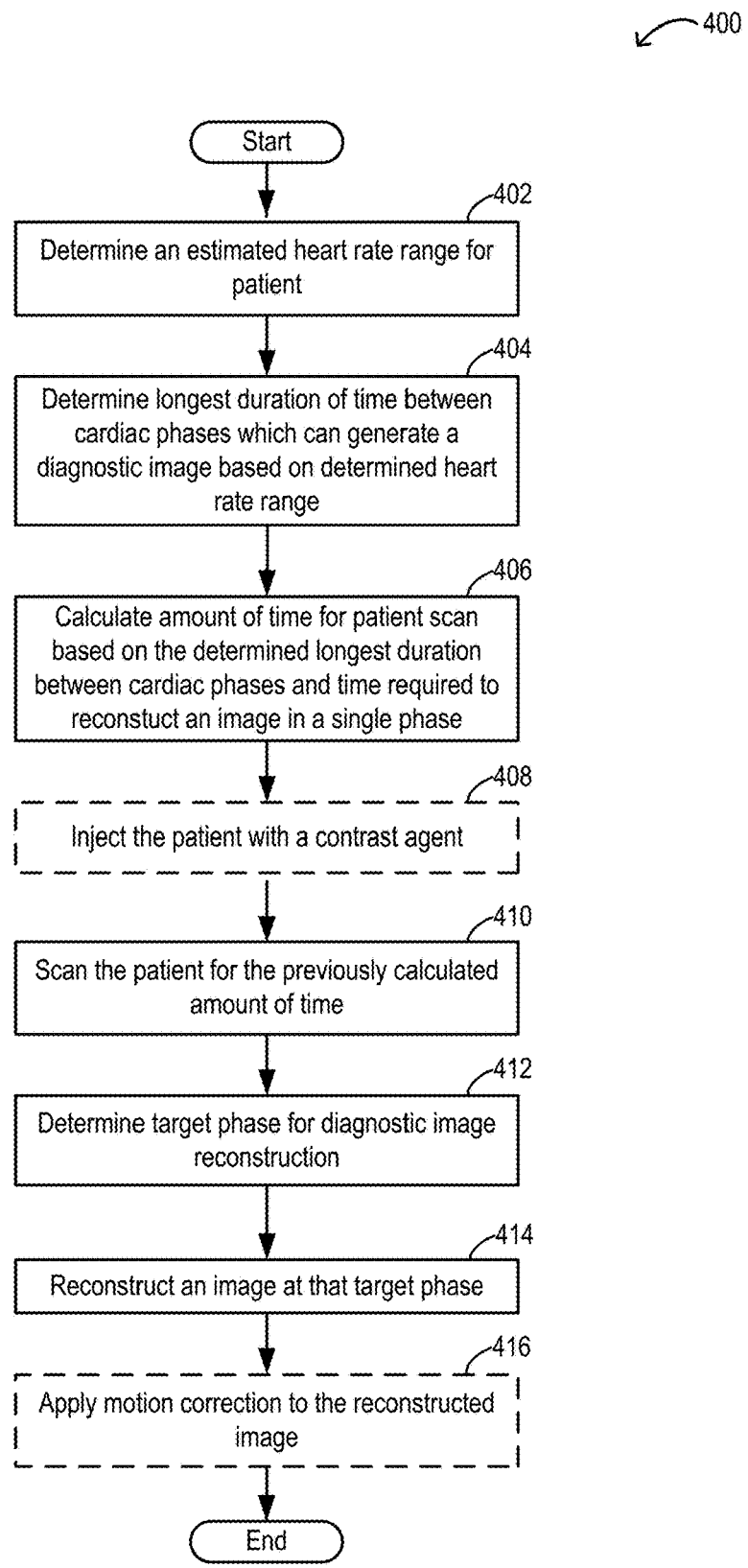
FIG. 4 provides a flow chart for performing a cardiac CT scan independent of a current phase of a cardiac cycle of a heart of a patient.

FIG. 4 is a flow chart showing a method 400 for generating a diagnostic cardiac image based on a model of heart rate motion. Method 400 may be executed by computer readable instructions stored in non-transitory memory of a computing device of a CT imaging system, such as computing device 216. Method 400 may begin at 402. At 402, method 400 may include determining an estimated heart rate range (e.g., 60-80 bpm, 70-90 bpm) for patient. For example, as part of the patient workflow, the patient's vital signs may be assessed and the patient's heart rate noted in an electronic medical record (EMR) before CT imaging. Computing device 216 may be in communication with an EMR database to access the patient's heart rate range data. In other embodiments, data from a heart rate monitor currently monitoring the patient may be sent directly to computing device 216. Alternatively, an operator may input data specifying the patient's heart rate range into operator console 220 which is communicatively coupled to computing device 216 or directly input patient heartbeat data into computing device 216.

A normal resting heart rate for adults typically ranges from 60 to 100 bpm, however many factors can influence heart rate (e.g., fitness level, age, emotions). For example, a well-trained athlete may have a resting heart rate range from 40-45 bpm before going into a CT scan whereas a chronic smoker who suffers from acute anxiety may have a resting heart rate ranging from 140-160 bpm. If the patient's heart rate is determined to be higher than typical (e.g., ranging from 150-170 bpm) or irregular, computing device 216 may send a notification to display 232 that further assessment may be performed by a medical professional to determine whether a beta-blocker may be administered to the patient. By administering a beta-blocker to the patient, a low and regular heart rate may be achieved thereby optimizing the patient's heart rate range to limit motion artifacts during the CT scan.

If a beta-blocker may be safely dispensed (e.g., orally and/or intravenously without any contraindications) to the patient, a medical professional may administer the beta-blocker and subsequently determine the patient's heart rate range once the medication has taken effect. Alternatively, a patient's heart rate may be estimated to be within a range instead of specifically determined (e.g., within a small low range such as 70-80 bpm or a within a wider range such as 40-120 bpm based on factors such as age, body size, general fitness). Data specifying the patient's determined heart rate range may then be sent to computing device 216 as previously described. Once a heart rate range has been determined for a patient, method 400 may then continue to 404.

At 404, a longest duration of time between cardiac phases which can generate a diagnostic image is determined based on the patient's heart rate range as determined at 402. As previously described with respect to FIGS. 3A and 3B, the least amount of cardiac motion happens within ventricular diastole which generally occurs during an R-R interval phase ranging from 45% to 100%. Thus, by acquiring projection data for a sufficient amount of time that either the end of systole or mid-diastole of an R-R interval will fall within the scan range regardless of when in the patient's cardiac cycle scanning commences it may be assumed that the exposure duration may robustly generate a diagnostic image. As previously described with respect to FIG. 3B, for a patient with systole ending at 45% and mid-diastole at 75%, in a worst case scenario, the longest duration between cardiac phases that will generate a diagnostic image is 70% of an R-R interval. Further, as the effect of heart rate on diastolic duration is predictable from kinematic modeling and known cellular physiology, a model of cardiac motion may be used to more precisely determine diastolic/systolic event times, with these precise event times then used for exposure time determinations. For example, based on heart rate range and kinematic modeling, mid-diastole may be found to occur at 85% for a patient rather than a generalized 75%. Thus, the longest duration between cardiac phases that may generate a diagnostic image would be from 85% to 145% rather than 75% to 145% and, as such, the required window of acquisition during scanning may be 60% of an R-R interval (as opposed to 70% when diastolic/systolic event times are not precisely determined).

As a non-limiting example, in patients with no evidence of heart disease, a linear relationship exists over the physiologic range of a resting heart rate between the duration of electrical systole (a QT interval) as well as total electromechanical systole (QS) and the heart rate. Further, the linear relationship between the QT interval and heart rate parallels that between the QS and heart rate. Thus, equations based on the regression lines for the relationship between QT or QS and heart rate over time may be used to determine precisely when a patient is in ventricular diastole based on heart rate. For example, the linear relationship between QS and heart rate may be modeled by the equation QS msec=541−2.2*heart rate. Thus, for a patient with a resting heart rate of 60 bpm, instead of assuming a general phase of 45%, the time to the end of systole may be better modeled as 541−2.2*60 which equals 409 msec or a phase of 40.9% ((409 msec/(60 sec/60 bpm)*1000 msec)*100%=40.9%). For a heart rate of 80 bpm the end of systole may occur at 48.7%, as 541−2.2*80=365 msec and (365 msec/(60 sec/80 bpm)*1000 msec)*100%=48.7%. Similarly, the time from an R-wave to the end of the early motion of diastole and the time from an R-wave to the start of the atrial contraction (near the end of ventricular diastole) may be modeled and appropriate cardiac CT timings constructed to fall within that ventricular diastole window based on a the patient's heart rate range as determined at 402.

Once a patient's cardiac event times (e.g., the end of systole, the middle of diastole) have been precisely determined using algorithms (stored in the non-transitory memory of computing device 216) based on kinematic cardiac modeling with regard to the patient's heart rate range as determined at 402, the event times (e.g., beginning or mid-diastole) may be used to determine the longest duration of time between the diagnostic cardiac phases (e.g., the phases which exhibit the least amount of cardiac motion and thus can robustly generate a diagnostic image if data is acquired at those times). For example, a patient with a heart rate ranging from 80-85 bpm may precisely end systole/begin diastole within a phase ranging from 47.2% to 48.7% based on the model of cardiac motion as described above. As such, mid-diastole may occur from 77.2% to 78.7%. Thus, in a worst case scenario, acquiring data long enough to ensure that either the end of systole or middle of diastole falls within the scan range may demand a scan duration of 67.8% of an R-R interval as 145%−77.2%=67.8%. Thus, the longest duration between the cardiac phases that may generate a diagnostic image is 67.8% for a determined heart rate range of 80-85 bpm.

Further refinements of cardiac motion may be used, incorporating for example the duration of the early filling of the ventricles, and thus utilizing a wider period of motion-free diastasis in the middle of diastole, such as 70-80% or even 65-80% at lower heart rates. Additionally, periods with higher amounts of motion may be used for the generation of diagnostic images if the motion correction algorithm is sufficiently good. For example, motions are generally higher in systole, but the motion pattern is generally smooth, so that motion correction algorithms may be sufficiently good to correct these phases and thus the associated intervals may be considered as sufficient to generate diagnostic images, thereby further reducing the interval required scanning. For example, if 20-30%, 40-50%, and 70-80% are all considered phases at which diagnostic images can be generated, then the longest duration between these phases is 80% to 120%, meaning that a scan of 40% plus the minimum scan time for one phase with motion correction, would be a sufficient scan duration.

The longest duration of time between the cardiac phases which can generate a diagnostic image may be determined using a look-up table programmed within reference values of phase percentages as a function of determined heart rate ranges programmed into the non-transitory memory of computing device 216, with computer output to include the longest interval in which at least the start of diastole or mid-diastole is included. Once this longest duration has been determined, method 400 may then continue to 406.

At 406, the amount of time for the patient scan is calculated based on the determined longest duration between the cardiac phases that may generate a diagnostic image determined at 404 and the time required to reconstruct an image in a single phase. As previously described with respect to FIGS. 1 and 2, gantry 102 and the components mounted thereon may be configured to rotate about center of rotation 206 for acquiring projection data, with rotational speed and/or position of the gantry 102 based on imaging requirements. Gantry rotation time is defined as the amount of time required to complete one full rotation (360°) of the x-ray tube and detector around the subject. As optimal temporal resolution during cardiac imaging is limited by the gantry rotation time, and the faster the gantry rotation, the greater the temporal resolution that may be achieved. In the past, the minimum rotation time was as high as 2 seconds; however, recent technological advances have decreased the gantry rotation time to less than 400 msec and as low as 280 msec. In one example, the minimum amount of projection data required to reconstruct a complete CT image may be 1800 of gantry rotation plus the fan beam angle (e.g., 30°, 60°, or 90°) of the CT detectors in the axial plane as the remaining 180 are a mirror image of the first.

Thus, the time required to reconstruct an image in a single phase may be determined based on gantry rotation speed and the degrees of acquisition demanded (e.g., a minimum of 180° of gantry rotation plus the fan beam angle). By combining the time required to reconstruct an image in a single phase with the determined longest duration between the cardiac phases that may generate a diagnostic image using an equation stored within the non-transitory memory of computing device 216, the amount of time for a patient scan may be calculated. The calculated time thus being of a sufficient duration to ensure that at least mid-diastole is centered within the acquisition window. For example, as described previously, the determined longest duration between cardiac phases that can generate a diagnostic image for a heart rate range of 80-85 bpm may be 67.8%. Thus, performing a partial scan demanding 240 of acquisition on a nominal CT scanner with a gantry speed of 280 msec for a patient with a heart rate range of 80-85 bpm would demand a total scan time of 0.6925 seconds as ((60/80)*0.678)+0.28 (240/360)=0.6925.

Once the amount of time for a patient scan has been calculated, dependent on the reason for cardiac CT imaging, method 400 may continue to optional step 408 or continue to 410. If vascular imaging is to be performed (e.g., for a coronary CT angiography (CTA)), computing device 216 may output a notification to an operator for method 400 to continue at 408 based on the patient's EMR data. Alternatively, if a patient is undergoing a cardiac calcium scoring scan or non-vascular images of the heart are needed for diagnosis, method 400 may continue at 410.

At 408, the patient may be injected with an intravenous contrast agent administered by a medical professional in response to a notification issued by computing device 216. Contrast agents are radio-opaque substances that may enhance the visibility of CT images by temporarily changing the way x-rays interact with internal structures of the body. When introduced into the body prior to an imaging exam, contrast agents make certain structures or tissues in the body appear different on the CT images than they would if no contrast material had been administered. Thus, contrast agents help distinguish selected areas of the body from surrounding tissue thereby improving visibility for diagnosis. As a non-limiting example, at 408, a patient may be given an intravenous injection of an iodinated contrast agent so that the coronary arteries are distinctly visible from the rest of the heart tissue within a CTA scan, thereby aiding in the diagnosis of potential causes of chest pain. Alternatively, a gadolinium-based contrast agent may be intravenously injected to better visualize the heart vasculature during a CTA scan. Once the contrast agent is at an optimal location and concentration to allow visualization of the coronary arteries, as determined by operator input into computing device 216 or via a monitoring device communicatively coupled to computing device 216, method 400 may continue at 410. In other embodiments, a contrast agent may be injected at any suitable time, including prior to calculation of the scan time at least in some examples.

At 410, the patient may be scanned for the previously calculated amount of time determined at 406 (e.g., a scanning duration). Computing device 216 may control the CT system, such as CT system 100 and imaging system 200 of FIGS. 1 and 2, during the patient scan. In an alternative embodiment, computing device 216 may output the time required for the patient scan to an operator who inputs the time command and/or scanning parameters to operator console 220 which is operatively coupled to the CT/imaging system. The scanning is initiated independent of the patient's current cardiac cycle phase (e.g., scanning may begin any point within ventricular systole or diastole) and without input from an ECG monitor. For example, scanning may commence in response to a request from an operator of the CT system to commence scanning, or scanning may commence automatically in response to the CT system determining that the patient is ready to be scanned. Thus, scanning may occur at any point within (independent of) the cardiac cycle (e.g., within a T-wave, just after a QRS complex). In some example, for a first scan, scanning begins before a specific point in the cycle, in a subsequent scan of the same patient, scanning begins after that same specific point in the cycle, and in another subsequent scan of the same patient, scanning begins before the specific point in the cycle, and so on, in that the system's automatic determination of scanning commencement is not made based on aligning the scanning to be at defined point of the cycle, and further is not synchronized with the heart's cycle. To initiate the scanning, the x-ray source(s) of the CT system are activated and the gantry is rotated. The detectors of the CT system detect the x-rays that pass through the patient and the DAS 214 acquires projection data from the detectors. In some examples, the table supporting the patient may also be moved to initiate the scan. The x-ray source activation, gantry rotation, and detector output sampling may only occur for the calculated amount of time (e.g., the scan duration) and may terminate when the calculated amount of time has elapsed. In this way, projection data may be obtained only during the scanning duration and may not be obtained after the scanning duration has ended.

At 412, a target phase for diagnostic image reconstruction may be determined using algorithms stored in the non-transitory memory of computing device 216. The target phase as used herein may be defined as the window of the acquired projection data that, during acquisition, the least amount of coronary motion occurs. In some embodiments, the determination of the target phase for reconstruction may be based on an amount of motion detected in the projection data, and phases/windows of the projection data having higher motion may be ignored for the purposes of image reconstruction, resulting in one or more images being reconstructed from projection data determined to have lower motion (e.g., the target phase). For example, an algorithm may be employed that retrospectively develops an image metric for quantifying this target phase from the matrix of detector values generated during the patient scan. For example, image analysis algorithms in various embodiments may utilize a cost function that considers one or more of motion, contrast, image quality, or another image quality metric to determine a phase or phases having the least motion or otherwise providing an ideal, optimal, or preferred phase for final image reconstruction. In other embodiments, an automatic phase detection or selection algorithm may consist of two independently calculated metrics that quantify image quality and the metrics evaluated jointly to select the target phase for reconstruction. Further, in other examples, the acceptability threshold of the target phase may be adaptively adjusted during automatic phase detection through the application of motion correction.

In some examples, determining the target phase for reconstruction may be dispensed with, and all of the acquired data may be used for image reconstruction. In such examples, an operator of the CT system or other clinician may review each reconstructed image and select one or more images that include the target anatomy with little or no motion to be saved as a diagnostic image (e.g., as part of the patient's exam). However, by automatically determining which data to reconstruct the images from to only generate images that have little or no motion, operator workflow may be improved.

At 414, an image may be reconstructed at that target phase using algorithms stored as executable instructions within the non-transitory memory of image reconstructor 230 and/or computing device 216 as previously described with respect to FIG. 2. The target phase may be used to reconstruct a tomographic image of the heart or its vasculature using a suitable reconstructive technique, such as analytical or iterative reconstruction (IR) methods (e.g., filtered back projection). The reconstruction technique may be based on the type of projection data collected by the CT system. If the image reconstructed at that target phase contains coronary motion artifacts and is thereby deemed insufficient for diagnosis, method 400 may continue to optional step 416. Alternatively, if the reconstructed image is sufficient for diagnostic purposes (e.g., motion correction is not desired), computing device 216 and/or image reconstructor 230 may transmit the reconstructed image to display 232 and/or storage device 218 and method 400 may end.

At 416, motion correction may be applied to the reconstructed image generated at 414. In one embodiment, a motion correction algorithm may use an autofocusing method in which optimization-based refining of the image is performed with respect to some quality measure. In other examples, an algorithm may iteratively search for the motion trajectory yielding the sharpest image as measured by the entropy of spatial gradients. In other embodiments of method 400, application of a motion correction algorithm to reduce and/or remove motion artifacts in the image data may be performed during target phase determination at 410 or performed prospectively during scanning. Once the reconstructed image is sufficient for diagnostic purposes following the application of motion correction, computing device 216 and/or image reconstructor 230 may transmit the reconstructed image to display 232 and/or storage device 218 and method 400 may end.

Thus, method 400 may provide for one or more images of a patient's heart to be reconstructed from projection data collected over a scanning duration that is less than a single heartbeat of the patient's heart, with scanning commenced independent of a current phase of the cardiac cycle of the patient's heart. In some examples, the one or more images may be reconstructed using projection data collected in a single acquisition (e.g. of the scanning duration), such as when the CT system has sufficiently wide spatial coverage to cover the whole heart so only one acquisition is needed. For CT systems with less coverage, different regions of the heart, such as the top, middle, and bottom, may be scanned in sequential time intervals (e.g., each of the scanning duration described herein) with a table move between each, with sufficient overlap so that all anatomy is covered by at least one scan. Alternatively, a helical scan of the heart may be done without ECG gating if motion correction is sufficiently robust. The helical pitch may be based on the cardiac intervals as described above (e.g., the longest non-diagnostic interval), so that each slice has sufficient times or phases available to support the reconstruction of at least one diagnostic image.

In this way, the limitations of and costs associated with cardiac CT systems that utilize ECG gating techniques may be overcome according to the method described herein. The embodiments disclosed herein allow for a reconstructed diagnostic image of a patient's heart to be obtained from a cardiac CT scan without the use of an ECG. By utilizing a model of patient cardiac motion to determine CT system scan timing and duration, the method herein allows for diagnostic images to be robustly generated regardless of a patient's geometry, trauma history, or ECG signal. The technical effect of performing cardiac CT scans based on a model of cardiac motion is that a diagnostic cardiac image may be generated in less than a heartbeat thereby decreasing patient exposure to radiation.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. Although the examples provided herein are related to medical application, the scope of the present disclosure covers non-destructive testing in industrial, biomedical, and other fields. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an x-ray imaging system, comprising:
   determining a scanning duration for scanning a heart of a patient with the x-ray imaging system based on a heart rate of the patient;
   scanning the patient with the x-ray imaging system for the scanning duration, the scanning commenced independent of a current phase of a cardiac cycle of the heart of the patient; and
   reconstructing an image from data acquired during the scanning,
      wherein determining the scanning duration based on the heart rate of the patient comprises determining a longest non-diagnostic interval of one or more successive cardiac cycles of the heart of the patient based on the heart rate of the patient.

2. The method of claim 1, wherein determining the scanning duration based on the heart rate of the patient comprises determining the scanning duration based on a measured or estimated heart rate of the patient.

3. The method of claim 1, wherein the longest non-diagnostic interval is defined as an interval from mid-diastole of a first cardiac cycle to end of systole of a second, subsequent cardiac cycle, wherein determining the longest non-diagnostic interval based on the heart rate comprises identifying when, in the first cardiac cycle, mid-diastole is predicted to occur and when, in the second cardiac cycle, the end of systole is predicted to occur and determining an amount of time from the identified mid-diastole to the identified end of systole based on the heart rate.

4. The method of claim 3, wherein identifying when, in the first cardiac cycle, mid-diastole is predicted to occur and when, in the second cardiac cycle, the end of systole is predicted to occur comprises identifying when mid-diastole is predicted to occur and when the end of systole is predicted to occur based on the heart rate of the patient.

5. The method of claim 1, wherein determining the scanning duration based on the heart rate of the patient further comprises determining a duration of the longest non-diagnostic interval based on the heart rate and adding a predefined minimum scan duration to the duration of the longest non-diagnostic interval to generate the scanning duration.

6. The method of claim 1, wherein scanning the patient with the x-ray imaging system for the scanning duration comprises commencing scanning of the patient at a beginning of the scanning duration and terminating scanning of the patient at an end of the scanning duration.

7. The method of claim 6, wherein the x-ray imaging system is a computed tomography (CT) x-ray imaging system, and wherein commencing scanning of the patient comprises activating one or more x-ray sources of the CT x-ray imaging system and/or moving a table of the CT x-ray imaging system supporting the patient.

8. A method for an x-ray computed tomography (CT) imaging system, comprising:
   determining a scanning duration based on a measured or estimated heart rate of a patient;
   responsive to a scan command that is independent of a current phase of a cardiac cycle of a heart of the patient, scanning the heart of the patient with the x-ray CT imaging system for the scanning duration;
   the scanning duration shorter than a duration of a single cardiac cycle of the patient and longer than a minimum scanning duration for reconstructing a single image; and
   reconstructing an image from data acquired during the scanning.

9. The method of claim 8, wherein the scan command is a command to commence scanning received via user input.

10. The method of claim 8, wherein determining the scanning duration based on the heart rate of the patient comprises identifying a first time within a first cardiac cycle of the patient at which mid-diastole is predicted to occur based on the heart rate and a second time within a second, subsequent cardiac cycle of the patient at which end of systole is predicted to occur based on the heart rate, and determining the scanning duration based on a duration from the first time to the second time.

11. The method of claim 10, wherein determining the scanning duration based on the duration from the first time to the second time comprises adding the duration from the first time to the second time to the minimum scanning duration in order to generate the scanning duration, the minimum scanning duration based on gantry speed and/or subsequent image processing parameters.

12. The method of claim 11, wherein when the subsequent image processing parameters include an indication that motion correction is to be applied to the image, the identification of the first time and identification of the second time includes identifying a first time range around when the mid-diastole is predicted to occur and identifying a second time range around when the end of systole is predicted to occur, and determining the scanning duration based on a duration from an end of the first time range to a beginning of the second time range and the minimum scanning duration.

13. The method of claim 11, wherein when the subsequent image processing parameters include an indication that motion correction is to be applied to the image, scanning the heart of the patient with the x-ray CT imaging system includes scanning the heart of the patient with the x-ray CT imaging system at a first gantry speed, and
   wherein when the subsequent image processing parameters include an indication that motion correction is not to be applied to the image, scanning the heart of the patient with the x-ray CT imaging system includes scanning the heart of the patient with the x-ray CT imaging system at a second gantry speed, higher than the first gantry speed.

14. A system, comprising:
   an x-ray source that emits a beam of x-rays toward a patient to be imaged;
   a detector that receives the x-rays attenuated by the patient;
   a data acquisition system (DAS) operably connected to the detector; and
   a computing device operably connected to the DAS and configured with executable instructions in non-transitory memory that when executed cause the computing device to:
      activate the x-ray source for a duration based on a heart rate of a heart of the patient, wherein the activating of the x-ray source is commenced independent of a phase of a cardiac cycle of the heart of the patient;
      acquire, via the DAS, projection data of the patient over the duration; and
      reconstruct, from the projection data, an image of the heart,
         wherein the duration is shorter than a duration to complete a single cardiac cycle of the patient and longer than a minimum scanning duration for reconstructing a single image.

15. The system of claim 14, wherein the instructions, when executed, cause the computing device to deactivate the x-ray source upon the duration having elapsed.

16. The system of claim 14, wherein the projection data acquired over the duration includes at least one of projection data acquired during an end of systole of the heart of the patient and projection data acquired during mid-diastole of the heart of the patient.

17. The system of claim 14, wherein the x-ray source is activated in response to a request received from a user.

* * * * *